United States Patent [19]
Kriesel

[11] Patent Number: 5,858,005
[45] Date of Patent: Jan. 12, 1999

[54] SUBCUTANEOUS INFUSION SET WITH DYNAMIC NEEDLE

[75] Inventor: Marshall S Kriesel, St. Paul, Minn.

[73] Assignee: Science Incorporated, Bloomington, Minn.

[21] Appl. No.: 919,146

[22] Filed: Aug. 27, 1997

[51] Int. Cl.$^6$ .................................................. A61M 25/02
[52] U.S. Cl. .................................. 604/180; 128/DIG. 26
[58] Field of Search ............................ 604/93, 174, 180, 604/239, 257, 264, 272, 273, 412; 128/DIG. 6, DIG. 26

[56] References Cited

U.S. PATENT DOCUMENTS

| | | |
|---|---|---|
| 3,194,235 | 7/1965 | Cooke . |
| 3,289,675 | 12/1966 | Dunmire et al. ..................... 604/272 |
| 3,918,446 | 11/1975 | Buttaravoli . |
| 4,380,243 | 4/1983 | Kamen . |
| 4,397,641 | 8/1983 | Jacobs ..................................... 604/180 |
| 4,659,329 | 4/1987 | Annis ....................................... 604/180 |
| 4,743,231 | 5/1988 | Kay et al. ................................ 604/180 |
| 5,169,389 | 12/1992 | Kriesel .................................... 604/132 |
| 5,176,662 | 1/1993 | Bartholomew et al. . |
| 5,205,818 | 4/1993 | Kolber . |
| 5,257,980 | 11/1993 | Van Antwerp et al. . |
| 5,371,627 | 12/1994 | Conway .................................. 604/180 |
| 5,390,671 | 2/1995 | Lord et al. . |
| 5,449,349 | 9/1995 | Sallee et al. ............................ 604/180 |
| 5,527,288 | 6/1996 | Gross et al. . |
| 5,547,468 | 8/1996 | Simon et al. ........................... 604/272 |
| 5,695,462 | 12/1997 | Sutcu et al. ............................ 604/264 |

*Primary Examiner*—Ronald Stright
*Assistant Examiner*—Sharon Finkel
*Attorney, Agent, or Firm*—James E. Brunton

[57] ABSTRACT

A subcutaneous infusion set for the subdermal infusion of fluids which includes a housing having an internal chamber within which a uniquely configured infusion cannula is dynamically mounted. The cannula, which is generally spiral shaped, has a body portion that is disposed within the internal chamber and a pierceable portion which extends angularly outwardly from the base of the apparatus. With this construction, when the device is interconnected with a patient, normal movement by the patient will permit the cannula to move dynamically within the internal chamber while the base of the device which is removably affixed to the patient's skin remains completely stationary.

11 Claims, 5 Drawing Sheets

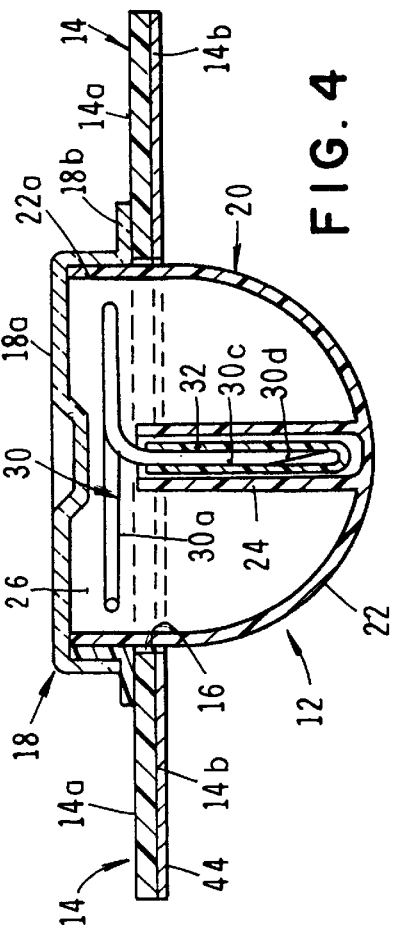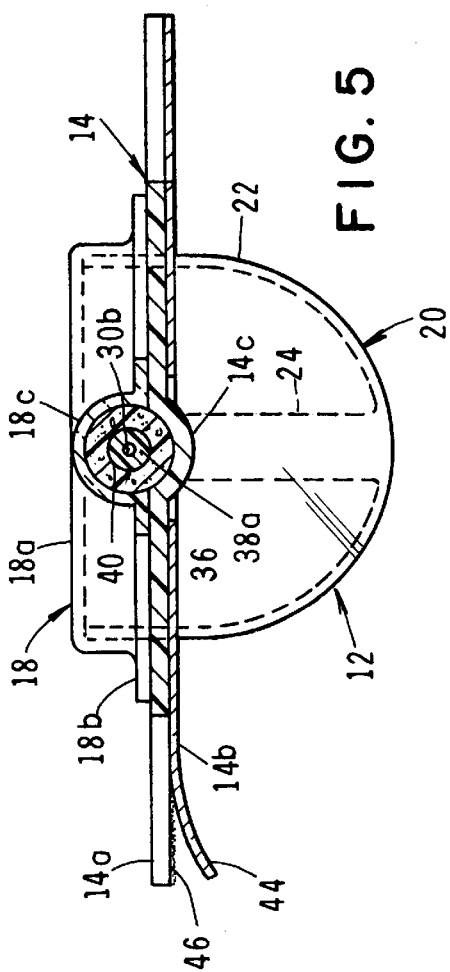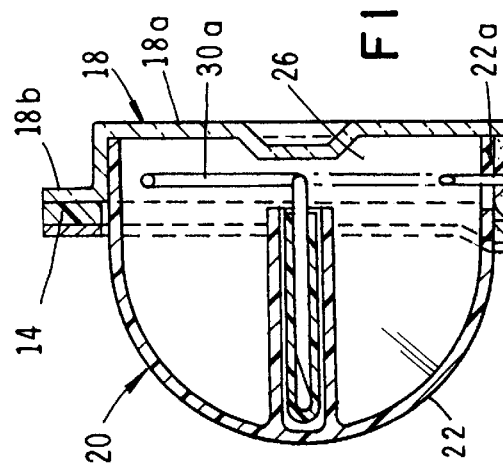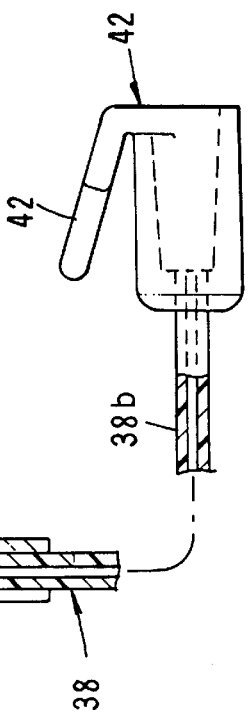

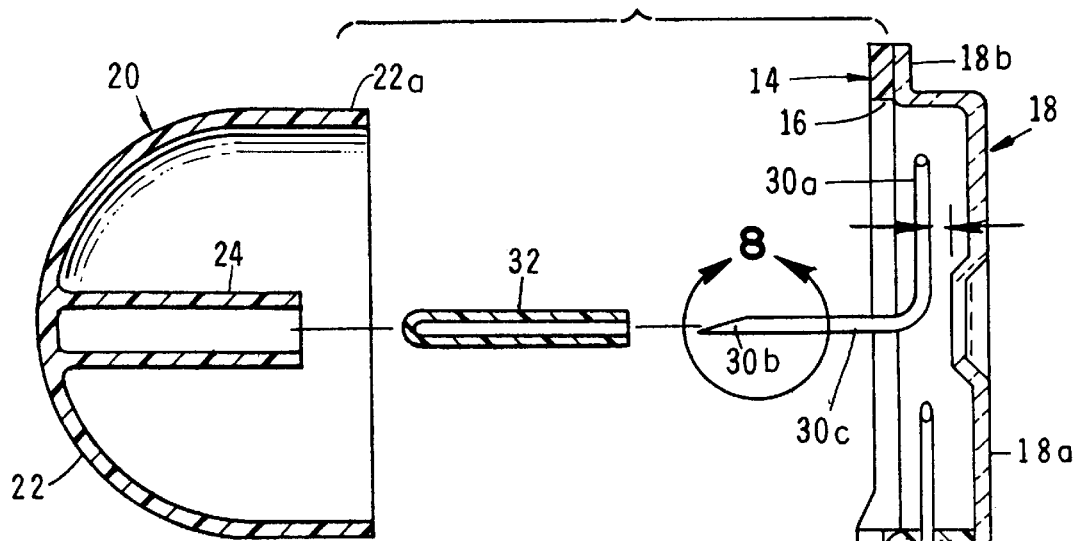
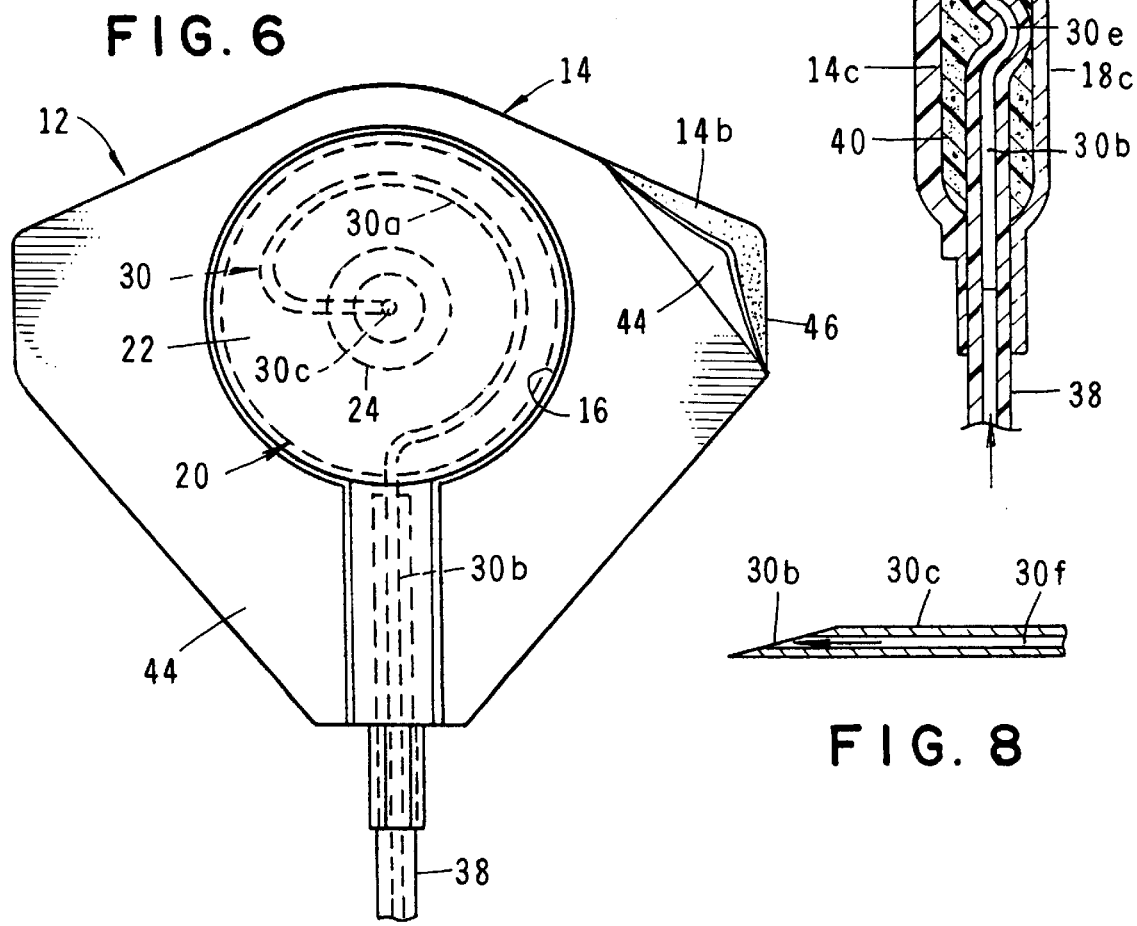
FIG. 6  FIG. 7  FIG. 8

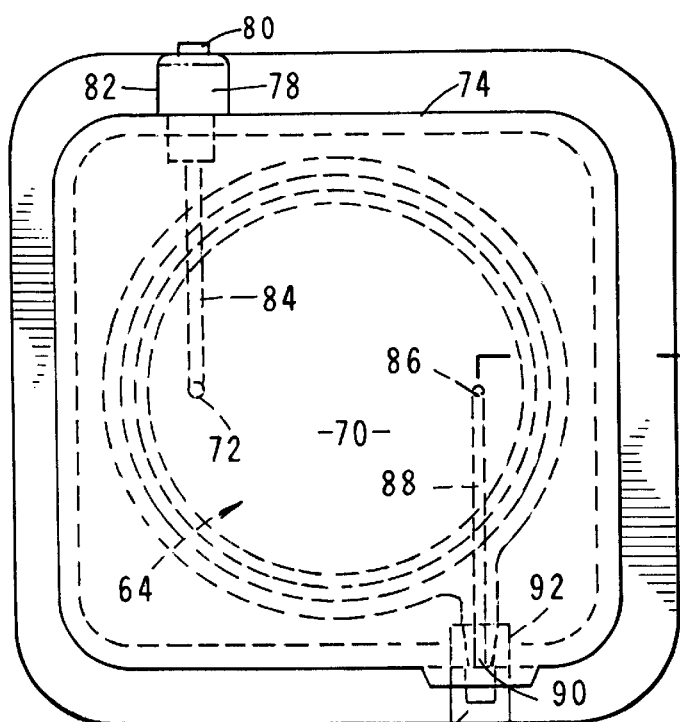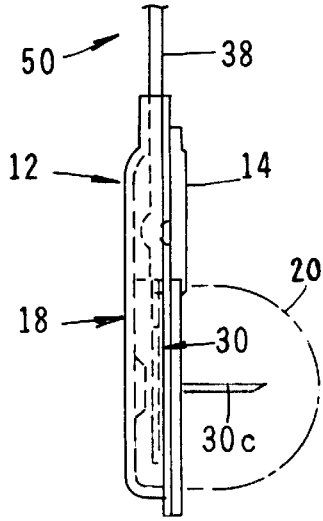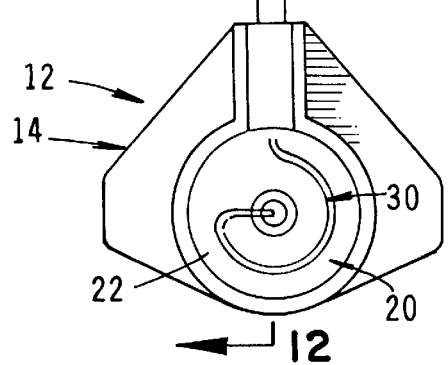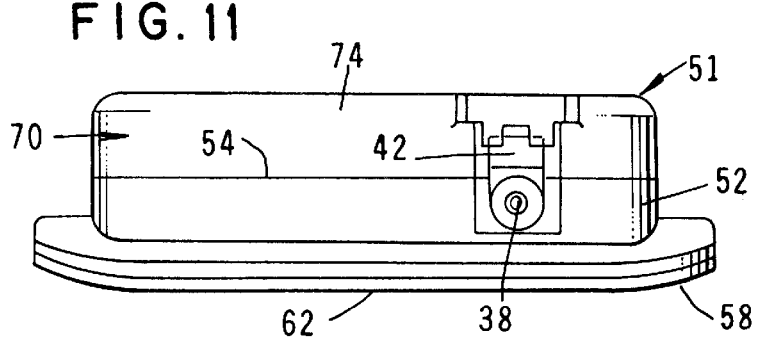

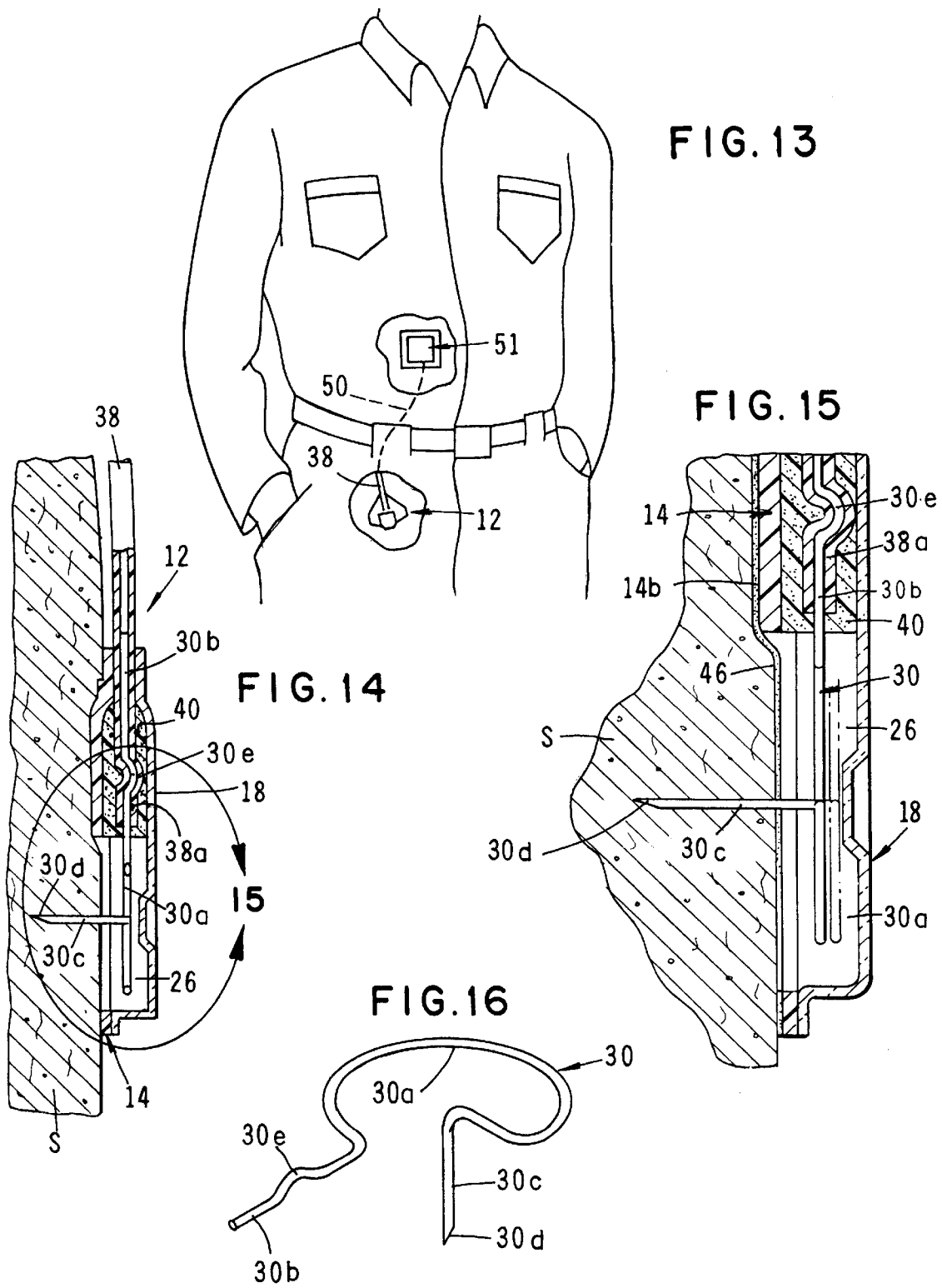

SUBCUTANEOUS INFUSION SET WITH DYNAMIC NEEDLE

BACKROUND OF THE INVENTION

Field of the Invention

The present invention relates generally to fluid delivery devices. More particularly, the invention concerns a subcutaneous infusion set with dynamic needle for interconnection with a source of medicinal fluid to enable subcutaneous delivery of the medicinal fluid to a patient.

DISCUSSION OF THE PRIOR ART

Subcutaneous injection sites are well know in the art for delivering selected medications to a desired subcutaneous site located beneath the skin of a patient. Typically, such injection sites comprise a relatively short catheter which is supported by a housing that is suitably interconnected with an external source of the medicament to be delivered to the patient. One such prior art device is described in U. S. Pat. No. 4,380,234 issued to Kamen. Another prior art subcutaneous infusion set of different construction is illustrated and described in U. S. Pat. No. 5,527,288 issued to Gross et al. Still a differently constructed subcutaneous infusion set is described in U. S. Pat. No. 5,176,662 issued to Bartholomew et al.

In a number of the prior art subcutaneous injection devices, the catheter is rigidly connected to a base and extends generally perpendicularly outward therefrom. In use, the base of the device is affixed to the patient's body by means of tape, an adhesive patch or the like. With this construction, each movement by the patient that causes flexing of the skin, muscles and tissues imparts undesirable loosening forces to the device which can cause the base of the device to become separated from the patient.

The thrust of the present invention is to overcome the drawbacks of the prior art subcutaneous injection devices by providing an injection site wherein the cannula is dynamically mounted to the base of the device in a manner such that normal movement by the patient will permit the cannula to move three dimensionally within a cavity formed in the base while the base itself remains completely stationary.

SUMMARY OF THE INVENTION

It is an object of the present invention to provide a subcutaneous infusion set for the subdermal infusion of fluids which is compact, easy to use and is of a highly novel construction in that it embodies a housing having an internal chamber within which a uniquely configured infusion cannula is dynamically mounted.

More particularly, it is an object of the invention to provide a novel subcutaneous infusion set of the aforementioned character which includes a novel and unique, generally spiral shaped delivery cannula having a body portion disposed within a chamber formed within the base superstructure of the apparatus and a pierceable portion which extends angularly outwardly from the base of the apparatus. By constructing the cannula in the novel spiral configuration, substantial structural stability of the cannula relative to the base is achieved as compared with prior art devices wherein a straight cannula protrudes from the base of the device.

Another object of the invention is to provide an infusion set of the character described in the preceding paragraphs in which, following interconnection of the device with a patient, normal movement by the patient will permit the cannula to move dynamically within the internal chamber while the base of the device remains completely stationary.

Another object of the invention is to provide, in combination with a novel subcutaneous infusion set of the character described, a novel fluid delivery apparatus which is compact, is of an extremely low profile and one which includes a self-contained stored energy membrane for expelling fluids toward the infusion set at a precisely controlled rate of flow.

It is another object of the invention to provide an apparatus of the aforementioned character which is small, highly reliable and easy to use by lay persons in a non-hospital environment.

A further object of the invention is to provide a low profile, fluid delivery device of the character described which includes a novel elastomeric membrane energy source which is of laminate construction and which can meet even the most stringent fluid delivery tolerance requirements.

Another object of the invention is to provide an apparatus of the character described which, due to its unique construction, can be manufactured inexpensively in large volume by automated machinery.

BREIF DESCRIPTION OF THE DRAWINGS

FIG. 1 is a generally perspective view of one form of the subcutaneous infusion set with dynamic needle of the present invention.

FIG. 2 is a top plan view of the infusion set illustrated in FIG. 1 and shown interconnected with a quick coupler element for coupling the device with a source of medicament.

FIG. 3 is a cross-sectional view taken along lines 3-3 of FIG. 2.

FIG. 4 is a cross-sectional view taken along lines 4-4 of FIG. 2.

FIG. 5 is a cross-sectional view taken along lines 5-5 of FIG. 2.

FIG. 6 is a bottom plan view of the infusion set shown in FIG. 1 and illustrating the manner in which the peel-off paper is peeled from the patient-engaging lower surface of the device.

FIG. 7 is a cross-sectional, exploded view similar to FIG. 3 but showing the removal of the protective cap assembly of the apparatus from the downwardly extending needle portion of the infusion set.

FIG. 8 is an enlarged, cross-sectional view of the area designated in FIG. 7 by the numeral 8.

FIG. 9 is a fragmentary, side-elevational view, partly in cross section of an alternate coupling element (a standard female luer) of the apparatus of the invention.

FIG. 10 is a top plan view of an alternate embodiment of the invention which comprises in combination a subcutaneous infusion set and a novel fluid delivery device for delivering medicament to the infusion set at a precise rate.

FIG. 11 is a front view of the fluid delivery device shown in FIG. 10.

FIG. 12 is a cross-sectional view taken along lines 12-12 of FIG. 10.

FIG. 13 is a generally illustrative perspective view showing the apparatus of this latest form of the invention attached to a patient.

FIG. 14 is an enlarged cross-sectional view of the subcutaneous infusion set portion of the apparatus shown in FIG. 13 illustrating the interconnection with the patient.

FIG. 15 is an enlarged fragmentary view of the area identified in FIG. 14 by the numeral 15.

FIG. 16 is a generally perspective view of the generally spiral shaped cannula of the subcutaneous infusion set portion of the apparatus.

DESCRIPTION OF THE DRAWINGS

Referring to the drawings and particularly to FIGS. 1 through 4, one form of the subcutaneous infusion device of the invention for infusing medicinal fluids into a patient is there shown and generally identified by the numeral 12. The device of this form of the invention comprises a base 14 having upper and lower surfaces 14a and 14b and a generally circular shaped opening 16 (FIGS. 2 and 4). Connected to upper surface 14a of base 14 is a cover 18 having a generally dome-shaped portion 18a, a flange portion 18b, and a stem portion 18c. Removably receivable within opening 16 is a generally dome-shaped closure assembly 20 which includes an outer wall 22 which terminates in a generally cylindrically shaped skirt portion 22a. Formed internally of wall 22 is a tubular-shaped, socket-like portion 24 (FIGS. 2 and 4), the purpose of which will presently be described.

Cover 18 and wall 22 cooperate to define a chamber 26 which houses the novel hollow cannula 30 of the invention. Cannula 30 includes a circuitously shaped body portion 30a which is disposed within chamber 26 and a stem portion 30b which is mounted within stem portion 18c of cover 18 in a manner presently to be described. Cannula 30 also includes an outlet end, here provided in the form of a needle-like segment 30c, which extends generally perpendicularly downward from lower surface 14b of base 14 for subdermal infusion of medicinal fluids into the patient. For this purpose, segment 30c is provided with a sharp, pointed extremity 30d (see FIG. 3). As also shown in FIG. 3, a protective sheath 32, which is telescopically received within socket-like portion 24, surrounds and protects segment 30c of the cannula.

Figure 1:
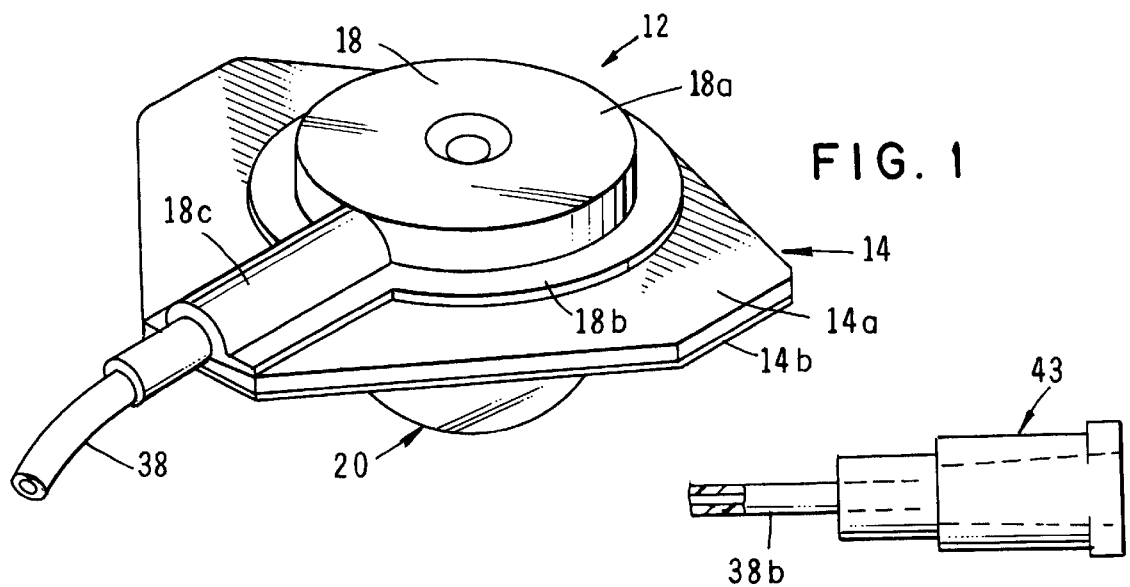
Figure 9:
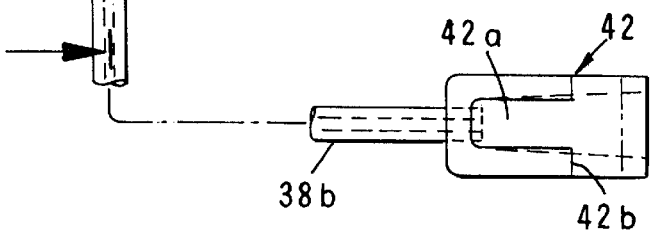
Figure 2:
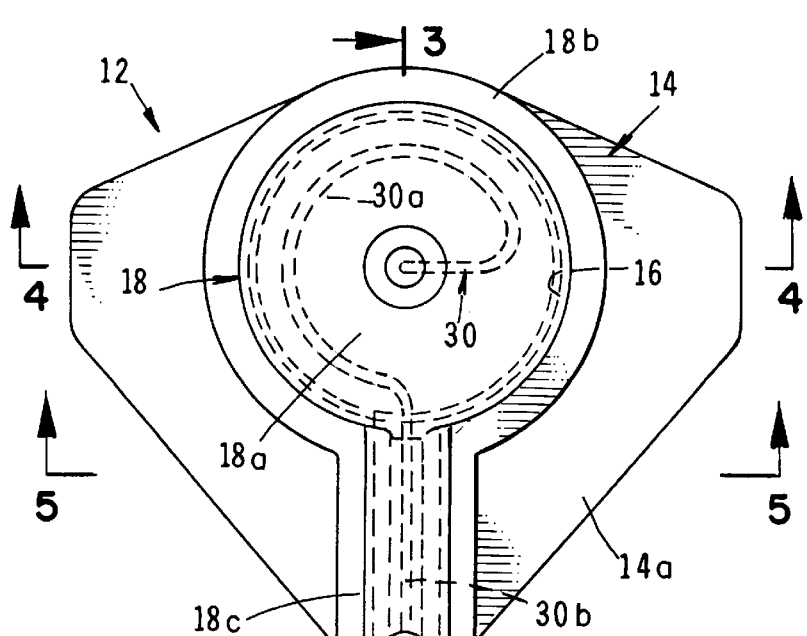

Turning particularly to FIGS. 3 and 5, it can be seen that stem portion 30b of the very small diameter spiral cannula 30 is encased within the inboard end 38a of a fluid delivery tube 38 and the assembly thus formed is uniquely supported between stem portion 18c of cover 18 and a concave segment 14c of base 14 by a cannula encapsulation means shown here as a standard potting compound 40. Compound 40 rigidly supports the inboard end of tube 38 and portion 30b of the cannula so as to provide a secure interconnection with base 14 and cover 18. As best seen in FIG. 3, portion 30b of the cannula is provided with a bend 30e to better secure the assemblage in place. Provided proximate outboard end 38b of delivery tube 38 is a quick connect member 42 which is usable with a standard type of male connector element to enable interconnection of the delivery tube 38 with a source of medicament (FIGS. 2 and 3). Quick connect member includes a locking lever 42a and a locking surface 42b (FIG. 2) adapted for locking engagement with the male connector element. An alternate form of connector a standard female luer usable with the device is shown in FIG. 9 and is generally designated by the numeral 43.

In using the device of the invention, after the luer connector has been suitably interconnected with a source of the medicament to be infused into the patient, closure assembly 20 is separated from base 14 and protective sheath 32 is slipped from end 30c of cannula 30. Next, the protective membrane covering 44 which protects the adhesive coating 46 provided on the lower surface 14b of base 14 is removed (see FIGS. 5 and 6). This done, the device can be interconnected with the patient by penetrating the patient's skin with the point 30d of the infusion cannula 30. As the infusion needle penetrates the patient's skin and tissue, the adhesive coated lower surface of base 14 will engage the patient's skin so as to hold the device securely in position.

An extremely important aspect of the apparatus of the invention resides in the novel design of the circuitous cannula 30 and its unique interconnection with the base 14 and cover 18. With the highly novel construction shown in the drawings, when the device is connected to the patient with the needle portion 30c of the cannula penetrating the patient's body, as, for example, the patient's arm or leg, normal movement by the patient will permit the cannula to move within chamber 26 while the base remains completely stationary. Without this important feature, normal movements by the patient causing flexing of the muscle and tissue would cause irritation and discomfort to the patient. Additionally, such movements could cause the small diameter cannula to fail catastrophically or could cause loosening of the adhesive bond which would result in separation of the device from the patient's skin. However, the novel and unique dynamic mounting of the cannula within chamber 26 positively prevents breaking of the frangible cannula and at the same time prevents irritation to the patient as a result of normal muscle flexing by the patient.

Referring to FIGS. 10 through 16, an alternate embodiment of the invention is there shown and generally designated by the numeral 50. The apparatus of this latest form of the invention comprises, in combination, a subcutaneous infusion set 12 of the character previously described and a novel fluid delivery device 51 for delivering fluids to the infusion set at a precise rate of flow. The subcutaneous infusion set portion of the apparatus is of identical construction to that shown in FIGS. 1 through 8 and like numerals have been used in FIGS. 10 through 16 to identify like components. The fluid delivery device is similar in some respects to the device described in U.S. Pat. No. 5,169,389 issued to the present inventor. Because of the pertinence of this patent, Pat. No. 5,169,389 is hereby incorporated herein by reference as though fully set forth herein.

As best seen by referring to FIGS. 10, 11, and 12, the fluid delivery device portion 51 of the apparatus comprises a base 52, having an upper surface 54 including a central portion 54a and a peripheral portion 54b circumscribing central portion 54a. As best seen in FIG. 12, base 52 is provided with a lower surface 56 to which a patient interconnection means or member 58 is connected. Member 58 functions to releasably interconnect the device to the patient and includes an adhesive layer 60 which is initially protected by a peel-away membrane 62.

The important stored energy means of the fluid delivery device 51 is here provided in the form of a laminate construction 64 comprising first and second elastomeric membranes 66 and 68 respectively which are interconnected about their peripheries with upper surface 54 of base 52. Laminate construction 64 is similar to that described in U.S. Pat. No. 5,169,389 which is incorporated herein by reference and is distendable as a result of pressure imparted on the construction by fluids "F" introduced into a fluid reservoir 70 through an inlet port 72 (FIG. 10). As the membranes 66 and 68 are simultaneously distended, internal stresses will be established, which stresses tend to move the laminate construction toward a less distended configuration and in a direction toward the upper surface 54 of base 52. In the manner shown in FIG. 11 and 12, cover 74 is superimposed over membranes 66 and 68 and is affixed to base 52 in a suitable manner such as by adhesive or sonic bonding.

Filling of reservoir 70 is accomplished by introducing fluid into the reservoir under pressure via a septum assembly 78 mounted in base 52. Septum assembly 78 includes a conventional pierceable septum 80 which is carried within a housing 82 that is connected to base 52. Using a conventional syringe assembly, fluid can be introduced into a fluid passageway 84 which terminates in the previously identified fluid inlet port 72. During this filling step, membranes 66 and 68 will distend outwardly as a unit toward the inner surface 74*a* of cover 74 in the manner best seen in FIG. 12.

Provided in base 52 is a fluid outlet port 86 which is in communication with an outlet passageway 88. Outlet passageway 88 terminates in a fluid outlet 90 formed in a male connector element or protuberance 92 which is adapted to lockably receive quick connect member 42 of the subcutaneous infusion set of the apparatus. Interconnection of quick connect member 42 with connector protuberance 92 places reservoir 70 in fluid communication with spiral cannula 30 via delivery tube 38 (see FIGS. 10 and 11).

Turning to FIGS. 14 and 15, the subcutaneous infusion device 12 which forms a part of the apparatus of this latest form of the invention, is of identical construction to that shown in FIGS. 1 through 8. As before, the device comprises a base 14 and a cover 18 which together define an internal chamber 26 within which a generally spiral shaped cannula 30 is dynamically mounted in the manner previously described. When infusion device 12 is interconnected with the fluid delivery device 51, using quick connect member 42 in the manner shown in FIGS. 10, 12, and 13, reservoir 70 is in fluid communication with the internal bore 30*f* (FIG. 8) of cannula 30 via delivery tube 38 and fluid passageway 88 formed in base 52.

Either before or after the infusion device 12 is suitably interconnected with the fluid delivery device 51, the fluid to be delivered to the patient is introduced into reservoir 70 using a conventional syringe. The closure assembly 20 is then separated from base 14 and protective sheath 22 is slipped from end 30*c* of cannula 30. Next, the protective membrane covering 44, which is provided on the lower surface of the base and which protects the adhesive coating, is removed (see FIGS. 5 and 6). This done, the device is interconnected with the lower abdomen of the patient by penetrating the patient's skin "S" with the point 30*d* of the infusion cannula 30 (see FIG. 14). As the patient's skin and tissue is penetrated by the infusion needle in the manner shown in FIGS. 14 and 15, the adhesive coated lower surface of base 14 will engage the patient's skin to hold the device securely in position. As previously mentioned, when the infusion device is connected to the patient in the manner shown in FIGS. 14 and 15, the unique dynamic mounting of the cannula within chamber 26 positively prevents breaking of the frangible cannula and at the same time prevents irritation to the patient as a result of normal muscle flexing by the patient.

With the subcutaneous infusion device interconnected with the patient, the peel strip 62 is removed from the base 52 of the delivery device and the delivery device is affixed to the patient's upper abdomen in the manner shown in FIG. 13 with the fluid reservoir 70 in communication with cannula 30, as the distendable membrane laminate 64 tends to return to its less distended starting position, the fluid "F" contained within reservoir 70 will be urged outwardly of the reservoir into passageway 88 via fluid outlet 86. The fluid will then flow through outlet 90 of the protuberance 92, into delivery tube 38, into bore 30*f* of the cannula 30 and then into the patient at a flow rate determined by the character of elastomeric membranes 66 and 68 which make up the laminate 64.

Distendable membranes 66 and 68 can be manufactured from several alternate materials including rubbers plastics and other thermoplastic elastomers. These include latex rubber, polyisoprene (natural rubber), butyl rubber, nitrile rubber, other homopolymer, copolymers (random, alternating, block, graft, crosslink and starblock), mechanical poly-blends and interpenetrating polymer networks. Examples of materials found particularly well suited for this application include: silicone polymers (polysiloxanes), high performance silicone elastomers made from high molecular weight polymers with appropriate fillers added. These materials are castable into thin film membranes and have high permeability (which allows maximum transport of vapor and gas), high bond and tear strength and excellent low temperature flexibility and radiation resistance.

With respect to the base and cover components of the infusion device 12 and the fluid delivery device 51, a wide variety of materials can be used, including: metals, rubber or plastics that are compatible with the liquids they contact and are preferably not non-allergenic. Examples of such materials are stainless steel, aluminum, latex rubber, butyl rubber, nitrile rubber, polyisiprene, styrene-butadiene copolymer, silicones, polyolefins such as polypropylene and polyethylene, polyesters, polyurethan, polyamides and polycarbonates. Manufacturers of suitable materials include: Dow Corning of Midland, Mich.; General Electric of Schenectady, N.Y. and Shell Chemical Company of Houston, Tex.

Reference should be made to U.S. Pat. No. 5,169,389, which is incorporated herein by reference, for a more complete description of the materials that can be used in the construction of the fluid delivery device of the present invention. This patent will also provide additional details concerning the construction and method of operation of the fluid delivery device portion of the apparatus of the present invention.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An apparatus for subdermal delivery of fluid from a source of fluid to a patient at a controlled rate comprising a subcutaneous infusion device having a body portion provided with an internal chamber and including a hollow cannula connected to said body portion, said hollow cannula having:

(a) an inlet end portion in fluid communication with the source of fluid;

(b) a central body portion disposed within said internal chamber for movement therewithin with respect to said inlet end portion; and (c) an outlet end portion comprising a pierceable portion extending outwardly from said body portion for insertion into the patient, said outlet end portion also being movable with respect to said inlet end portion.

2. An apparatus as defined in claim 1 in which said body portion includes a base portion and a cover portion connected to said base portion, said inlet end portion of said hollow cannula being disposed between and connected to said base portion and said cover portion.

3. An apparatus as defined in claim 1 in which said hollow cannula is generally spiral shaped and in which said outlet end portion thereof extends generally perpendicularly outward from said body portion.

4. An apparatus as defined in claim 1 in which said source of fluid comprises a fluid delivery device connected to and separably movable with respect to said subcutaneous infusion device, said fluid delivery device comprising:

(a) a base having an upper surface and a lower surface engageable with the patient and a fluid passageway having first and second ends, said second end being interconnected with said inlet end portion of said hollow cannula; and (b) stored energy means for forming in conjunction with said base, a reservoir having an inlet and an outlet, said outlet being in fluid communication with said fluid passageway, said stored energy means comprising at least one distendable membrane superimposed over said base, said membrane being distendable as a result of pressure imparted by fluids introduced into said reservoir to establish internal stresses, said stresses tending to move said membrane toward a less distended configuration.

5. An apparatus as defined in claim 4 in which said fluid delivery device is interconnected with said subcutaneous infusion device by an elongated, flexible delivery tube.

6. An apparatus as defined in claim 4 in which said fluid delivery device further includes fill means for filling said reservoir.

7. An apparatus as defined in claim 5 in which said fill means comprises a pierceable septum mounted within said base.

8. An apparatus for subdermal delivery of fluid to a patient at a controlled rate comprising:

(a) a fluid delivery device comprising:
  (i) a base having an upper surface and a lower surface engageable with the patient and a fluid passageway in said base, said fluid passageway having first and second ends;
  (ii) stored energy means for forming in conjunction with said base, a reservoir having an outlet in communication with said first end of said fluid passageway, said stored energy means comprising at least one distendable membrane superimposed over said base, said membrane being distendable as a result of pressure imparted by fluid introduced into said reservoir to establish internal stresses, said stresses tending to move said membrane toward a less distended configuration; and (b) a subcutaneous infusion device connected to and spaced apart from said fluid delivery device for infusing medicinal fluid from said fluid reservoir of said fluid delivery device into the patient, said subcutaneous infusion device including a body having an internal chamber and a hollow cannula connected to said body, said hollow cannula having:
  (i) an inlet end portion in fluid communication with said second end of said fluid passageway of said base of said fluid delivery device;
  (ii) a central body portion disposed within said internal chamber for movement therewithin relative to said body; and
  (iii) an outlet end portion comprising a pierceable portion extending outwardly from said body for insertion into the patient.

9. An apparatus as defined in claim 8, further including cannula encapsulation means for encapsulating and immovably constraining said inlet end portion of said hollow cannula within said body and for dynamically supporting said outlet end portion of said cannula.

10. A device as defined in claim 8 in which said fluid delivery device and said subcutaneous infusion device are connected together by an elongated fluid delivery tube.

11. A device as defined in claim 8 in which said body of said subcutaneous infusion device includes a base and a cover connected to said base and cooperating therewith to define said internal chamber and in which said subcutaneous delivery device further includes a cover assembly removably connected to said base for covering said outlet end portion of said cannula.

* * * * *